United States Patent

Korpela et al.

Patent Number: 6,065,605
Date of Patent: May 23, 2000

[54] TWO-STAGE SEPARATION METHOD

[75] Inventors: Matti Korpela, Masala; Jukka Tuunanen, Helsinki, both of Finland

[73] Assignee: Labsystems Oy, Helsinki, Finland

[21] Appl. No.: 08/817,605

[22] PCT Filed: Oct. 20, 1995

[86] PCT No.: PCT/FI95/00580

§ 371 Date: Sep. 18, 1997

§ 102(e) Date: Sep. 18, 1997

[87] PCT Pub. No.: WO96/12961

PCT Pub. Date: May 2, 1996

[30] Foreign Application Priority Data

Oct. 20, 1994 [FI] Finland .................................. 944940

[51] Int. Cl.[7] .................................................. B03C 1/00
[52] U.S. Cl. .......................... 209/216; 210/222; 209/214
[58] Field of Search .................................. 209/214, 215, 209/216, 217, 223.1, 230; 210/222, 295

[56] References Cited

U.S. PATENT DOCUMENTS

| | | | |
|---|---|---|---|
| 2,471,764 | 5/1949 | Miller et al. | 294/65.5 |
| 3,904,482 | 9/1975 | Mehl | 195/109 |
| 3,970,518 | 7/1976 | Giaever | 195/1.5 |
| 3,985,649 | 10/1976 | Eddelman . | |
| 4,018,886 | 4/1977 | Giaever | 424/12 |
| 4,115,535 | 9/1978 | Giaever | 424/1 |
| 4,200,613 | 4/1980 | Alfrey et al. | 422/71 |
| 4,272,510 | 6/1981 | Smith et al. | 427/47 |
| 4,438,068 | 3/1984 | Forrest | 422/61 |
| 4,495,151 | 1/1985 | Ohyama et al. | 422/102 |
| 4,649,116 | 3/1987 | Daty et al. | 435/287 |
| 4,731,337 | 3/1988 | Luotola et al. | 436/526 |
| 4,751,053 | 6/1988 | Dodin et al. . | |
| 4,891,321 | 1/1990 | Hubscher | 435/293 |
| 4,895,650 | 1/1990 | Wang . | |
| 5,167,926 | 12/1992 | Kimura et al. | 422/67 |
| 5,200,084 | 4/1993 | Liberti et al. | 210/695 |
| 5,206,034 | 4/1993 | Yamazaki | 425/145 |
| 5,318,914 | 6/1994 | Matte et al. . | |
| 5,466,574 | 11/1995 | Liberti et al. | 435/5 |
| 5,474,742 | 12/1995 | Tuuninen | 422/63 |
| 5,647,994 | 7/1997 | Tuunanen et al. | 210/695 |

FOREIGN PATENT DOCUMENTS

| | | |
|---|---|---|
| 0027008 A1 | 4/1981 | European Pat. Off. . |
| 0186001 A2 | 7/1986 | European Pat. Off. . |
| 0042755 B1 | 8/1988 | European Pat. Off. . |
| 0 317 286 | 5/1989 | European Pat. Off. . |
| 0351857 | 1/1990 | European Pat. Off. . |
| 0 358 948 | 3/1990 | European Pat. Off. . |
| 0479448 | 4/1992 | European Pat. Off. . |
| 0 522 322 | 1/1993 | European Pat. Off. . |
| 2824742 A1 | 2/1979 | Germany . |
| 58-5656 | 1/1983 | Japan . |
| 58-5657 | 1/1983 | Japan . |
| 58-5658 | 1/1983 | Japan . |
| 63-5263 | 1/1988 | Japan . |
| 63-5265 | 1/1988 | Japan . |
| 63-5266 | 1/1988 | Japan . |
| 1414479 | 11/1975 | United Kingdom . |
| 2147 698 | 5/1985 | United Kingdom . |
| 2147898 | 5/1985 | United Kingdom . |
| WO 86/06493 | 11/1986 | WIPO . |
| WO 87/05536 | 9/1987 | WIPO . |
| WO 94/18565 | 8/1994 | WIPO . |
| WO 9418564 | 8/1994 | WIPO . |
| WO 95/00247 | 1/1995 | WIPO . |
| WO 9612958 | 5/1996 | WIPO . |
| WO 9612959 | 5/1996 | WIPO . |
| WO 9612960 | 5/1996 | WIPO . |
| WO 9612961 | 5/1996 | WIPO . |

*Primary Examiner*—Christopher P. Ellis
*Assistant Examiner*—Gene O. Crawford
*Attorney, Agent, or Firm*—Fish & Richardson P.C.

[57] ABSTRACT

In an embodiment, a separating member is introduced into the compound, the member comprising a separating surface, the particles are pulled from the compound, by using a magnetic field, to be adhered to a separating surface, the effect of the magnetic field is eliminated, and the particles (16) are collected thereafter from the separating surface. In this way, it is possible to collect particles effectively even from a large volume. It is also easy to transfer particles into a small volume. The invention can be employed in various applications, especially in the fields of biotechnology, biochemistry, and biomedicine.

17 Claims, 2 Drawing Sheets

TWO-STAGE SEPARATION METHOD

TECHNICAL FIELD

The invention relates to the separation of magnetic particles from a composition containing them. The invention can be used in different applications in the fields of biotechnology, biochemistry, and biomedicine.

TECHNICAL BACKGROUND BACKGROUND OF THE INVENTION

Magnetic microparticles are used as a solid phase in various applications to bind biomaterial. One advantage of microparticles is the large area of the solid phase and short diffusion lengths. The size of microparticles is generally 0.05–10 $\mu$m and they are available in different materials and already activated for many applications. Magnetic particles can be moved by using a magnet.

The separation methods of magnetic particles currently used include settling a reaction vessel in a magnetic field so that particles are accumulated into a so-called pellet at the bottom of the vessel. Thereafter, the liquid which is free from particles is removed by decantation or aspiration. However, removing the liquid from the vessel must be carried out very carefully so as not to remove the particles.

Publication EP-140787 (corresponding to publication U.S. Pat. No. 4,649,116) proposes a method by which micro-size magnetic particles are separated from a liquid by using a magnetic rod which is pushed thereto. The particles are pulled off the rod by using a stronger magnet.

Publication WO-86/06493 suggests a method to be used in immunoassays, in which magnetic particles and the marked complex adhered to them are separated from a liquid by using a magnetic rod and subsequently taken to be measured. The tip of the rod comprises a fixed magnet and a removable protective cover to whose outer surface the particles adhere. It is preferable to cover the protective cover with another cover after the separation and before measuring. After the measurement, the protective covers are detached, together with the particles, and thrown away and new covers are taken for a new separation. According to the publication, the magnet can also be an electromagnet, whereby the magnetic field can be eliminated when desired.

Publication WO-87/05536 suggests a device for separating magnetic particles, comprising, on the inside, a rod movable in a vertical boring and a magnet at the lower end thereof. The device is introduced, with the magnet in the lower position, into a liquid containing particles, whereby the particles are accumulated on the end of the rod. When the magnet is allowed into the upper position, the particles can be detached from the rod. In this way, particles can be collected and transferred from one liquid into another.

However, the disclosed separation methods of magnetic particles cannot be applied very well in objects of use in which particles must be collected from a fairly large volume compared with the separation device.

SUMMARY OF THE INVENTION

Now, a separation method according to claim 1 has been invented. The other claims present some preferred embodiments of the invention.

According to the invention, particles are separated from a composition so that the particles are first concentrated on the surface of a special separation body by using a magnetic field. In the second stage, the effect of the magnetic field is eliminated and the particles are collected from the surface of the separation body. In this way, particles can be collected effectively even from a large volume. It is also easy to transfer particles to a small volume.

A detachable magnet is preferably connected to the separation body. When separating particles from the compound, the magnetic member is in a position where a magnetic field pulls the particles onto the surface of the separation body. When collecting the particles from the surface of the separation body, the magnetic member is moved into a position in which it no longer influences the particles.

One or more grooves or the like can be provided on the surface of the body in which groove the particles are accumulated.

The separation body preferably has an elongated form. Consequently, the magnetic field inside it is preferably transversal to the separation body and wide in the longitudinal direction of the separation body. There are preferably grooves in the direction of the width of the field provided on the surface of the separation body against the ends of the magnet, the particles being accumulated in the grooves.

The particles can be collected from the surface of the separation body by using any suitable method, such as mechanical lifting off.

The collecting of particles is preferably carried out by using an elongated collecting member that comprises a longitudinal magnetic field, the strength and gradient of which are in their maximum at the end of the collecting member. The particles are thus accumulated in a concentrated manner at the end of the collecting member from where they can be detached even into a small volume. It is also easy to collect the particles in a concentrated manner by using such a separation member. The collection can be effected in the liquid when desired.

The magnetic field is preferably positioned at the end of the separation member by using a long rod magnet. The length of the rod magnet with respect to the thickness thereof is, e.g., at least about 2:1, preferably at least about 3:1, and most preferably at least about 12:1.

The rod magnet is preferably formed of a permanent magnet and a ferromagnetic arm which is provided as an extension of it. Thus the magnet and the magnetised arm together function as a long rod magnet. The arm dissolves the gradient of the upper pole of the field, whereby the upper pole does not carry out the collection of particles. By using the ferromagnetic arm, the long rod magnet can be provided at relatively low cost. However, even with the ferromagnetic arm, it is advantageous to use a relatively long magnet (with a length of, e.g., about 2 . . . 10 times the diameter). The length of the magnet is preferably chosen so that a maximum internal, permanent field strength is provided for the magnet in question. The junction between the magnet and the arm is preferably made so that the arm and the magnet come inside one another for a short distance. In this way, the formation of strong gradients at the junction, which may possibly collect particles, is avoided.

The cross section of the rod magnet can be, e.g., round or rectangular. The round shape is the best with respect to both manufacture and use. Indeed, the rotation of the magnet on its axis, for example, has no effect in this case. In principle, the rod can be curved to make the moving mechanisms simpler.

The particles can be detached from the magnetic collection member, when needed, by any suitable manner, even mechanically or by using another magnet. However, the particles are preferably detached by cancelling the effect of the magnetic field in the collection member. The collection member preferably comprises a protective cover and a rod with a magnet which is movable with respect to the cover.

The tip of the cover preferably comprises a sharp, downward oriented projection. This minimises the amount of liquid remaining at the tip. The tip is typically cone-shaped. When transferring particles into very small vessels, the tip is preferably the shape of a concave cone.

The shape of the collection member cover can vary according to the use. Normally, the round shape is the most advantageous with respect to both manufacture and use. In order to increase strength, the cover can be made conical, which also facilitates the manufacture of the cover by injection moulding.

The method can be applied in both simple manual tools and automatic multi-channel systems.

The invention is best adapted to be used for particles of about 1–10 μm.

BRIEF DESCRIPTION OF THE DRAWING

Some preferred applications of the invention are described in the following as examples. In the drawings of the description.

DETAILED DESCRIPTION OF THE INVENTION

Figure 1:
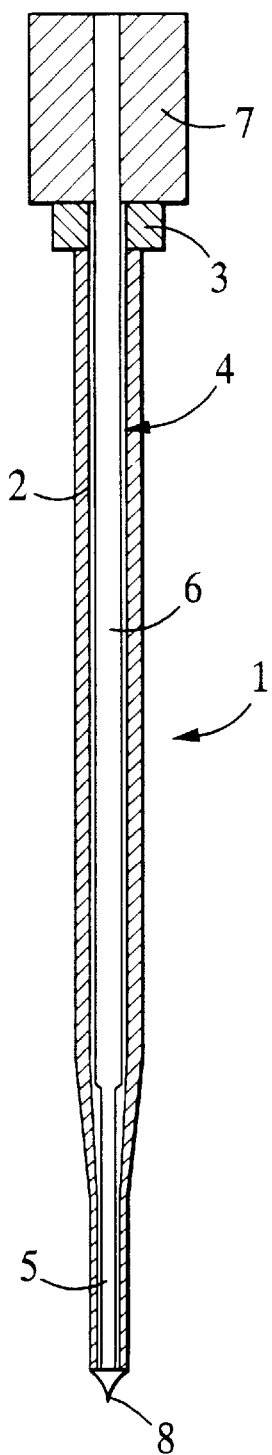
FIG. 1 presents a collecting member useful for the invention.

The separating rod according to FIG. 1 comprises elongated protective cover 1 and boring 2 in it. The lower ends of the cover and the boring are slightly tapered. The upper end of the frame comprises gripping nub 3.

Boring 2 comprises loose magnetic rod 4. This comprises vertical rod magnet 5 at the lower end thereof, and ferromagnetic arm 6 above it as an extension of the magnet. Gripping nub 7 is provided at the end of the arm.

The lower end of the cover is provided with tapering, sharp-ended tip 8 with a concave surface. The length of the tip corresponds approximately to the width of the lower end of the cover.

The proportion of the length of magnet 5 to its thickness is c. 10:1 and the proportion of the arm length to the length of the magnet is c. 5:1. The arm is slightly thicker than the magnet and the upper end of the magnet is embedded inside the lower end of the arm for a distance of about twice its thickness.

Tip 8 is especially well-adapted to transfer particles into a very small vessel, such as a so-called well of an HLA-plate. In this case the tip is slightly longer than the height of the well and the diameter of the upper part of the tip is slightly smaller than the width of the well. When the tip is pushed into the well, the surface of the liquid in it rises upwards under the influence of surface tension along the surface of the tip. The edge of the moving surface of liquid wipes the particles off the tip into the liquid. The detachment can be enhanced by moving the rod. Correspondingly, when the tip is lifted from the well, the surface of the liquid moves towards the sharp end of the tip as an integral membrane. In this way, the liquid and the particles along with it are completely detached from the tip.

Figure 3:
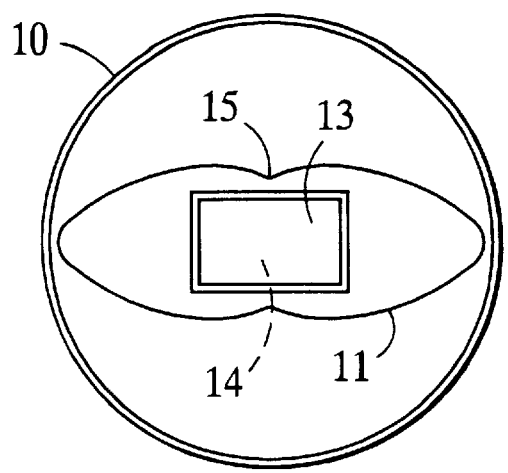
FIG. 3 presents the equipment of FIG. 2 from above.
Figure 2:
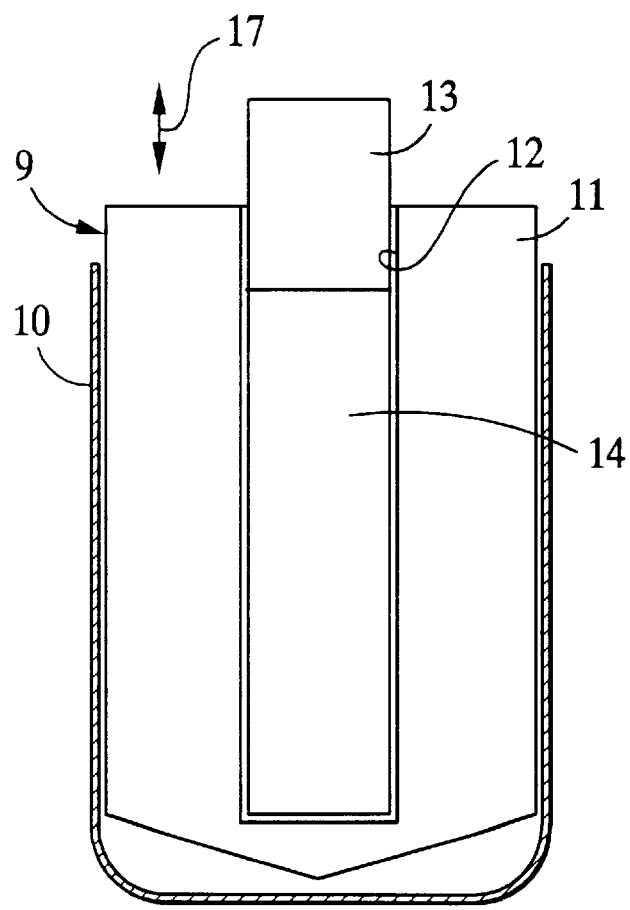
FIG. 2 presents the separating member of particles in a separating vessel as shown from the side.

FIGS. 2 and 3 present one separating member 9 according to the invention in a fairly high vessel 10 that contains magnetic particles as a liquid suspension. The separating member comprises body 11 that is slightly higher than the height of the vessel, recess 12 with a rectangular cross-section extending from the upper end of the body to the vicinity of the lower end. The recess comprises loose magnetic rod 13 that comprises magnet 14 at the lower end thereof. The field of the magnet is transversal to the recess (in FIG. 2 it is perpendicular to the plane of the image).

The basic form of the cross-section of body 11 is a fairly flat ellipse, each side of the ellipse being inwardly curved in the middle thereof so that the body comprises two longitudinal collecting grooves 15 against the ends of the magnet. The tip of the lower end of the body is sharp.

Figure 4:
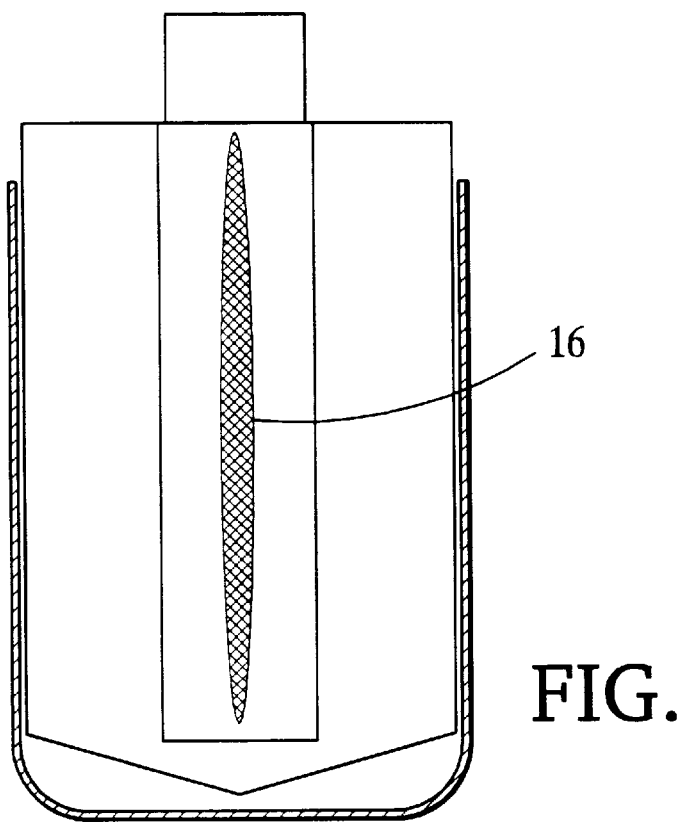
FIG. 4 presents the separation of particles from a composition.
Figure 5:
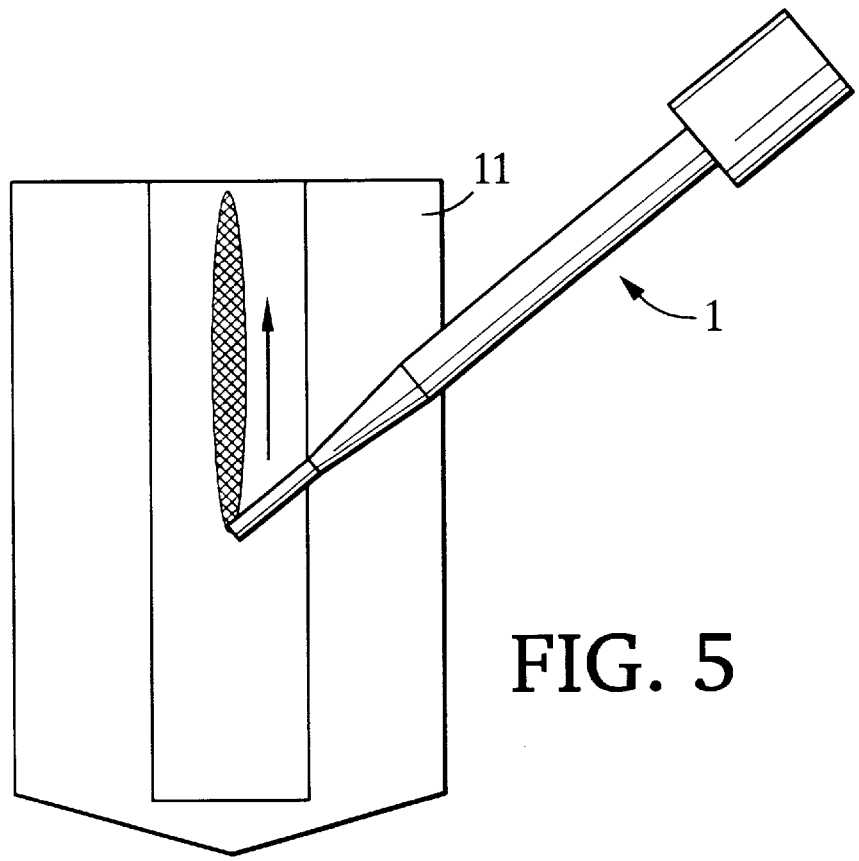
FIG. 5 presents the collection of particles from the separating member.

When rod 13 is in its recess 12, the magnetic particles are accumulated from the compound in vessel 10 into grooves 15, forming elongated strips 16 (FIG. 4). When the particles are to be detached, the rod is removed and the particles are collected from the grooves by using separating rod 1 (FIG. 5).

When the separating member is removed from the vessel, the amount of liquid and, consequently, impurities coming along with the particles is very small. However, the particles are so wet that it is easy to collect them from the surface of the member.

We claim:

1. A two-stage method of separating magnetic particles from a composition containing them, comprising the steps of:
   a. introducing a separating member comprising a separating surface into the composition,
   b. pulling particles from the composition, by using a magnetic field, to adhere to the separating surface,
   c. eliminating the effect of the magnetic field, and
   d. collecting the particles from the separating surface by using a separating rod to which the magnetic particles adhere.

2. A method according to claim 1, wherein the separating rod comprises an elongated body that comprises an upper end and a lower end, and a magnet is provided at the lower end of the body.

3. A method according to claim 2, wherein the separating rod comprises a magnetic rod in the same direction as the body, the proportion of the length of the rod to its thickness being at least about 2:1 preferably about 3:1, and most preferably about 12:1.

4. A method according to claim 3, wherein the magnetic rod comprises a magnet at the lower end thereof, a ferromagnetic arm being attached to the upper end of the magnet.

5. A method according to claim 1, wherein the particles are pulled onto the separating surface to form an elongated strip.

6. A method according to claim 5, wherein the particles are pulled to form a vertical strip.

7. A method according to claim 5 wherein the particles are pulled to form two strips on the opposite sides of the separating member.

8. A method according to claim 5, wherein the particles are pulled by using a magnet comprising a field oriented perpendicularly to the direction of the strip.

9. A device for separating magnetic particles from a composition containing them, comprising:
   (a) a separating member which is introduced into the composition for pulling particles onto the surface of the separating member by using a magnetic field, and (b) a collecting member comprising a separating rod to which the magnetic particles adhere.

10. A device according to claim 9, wherein the collecting member (1) comprises a protective cover.

11. A device according to claim 10, wherein the separating comprises a rod with a magnet movable with respect of the cover.

12. A method of separating magnetic particles from a composition, comprising introducing a separating member into the composition to pull said particles from the composition, said separating member including a magnetic member and a separating surface, the separating surface including a groove, and collecting the particles from the separating surface by using a separating rod to which the magnetic particles adhere.

13. The method of claims 1 or 12 wherein the particles are microparticles.

14. The method of claims 1 or 12 wherein the particles bind biomaterial.

15. The method of claim 12 wherein the groove is an elongated groove and the magnetic member is arranged to preferentially pull particles into the groove.

16. The method of claim 15 wherein said separating member introduces a magnet moveable relative to said separating surface.

17. The method of claim 16, comprising, eliminating the effect of the magnetic field prior to collecting the particles.

\* \* \* \* \*